US00PP23524P2

(12) United States Plant Patent
MacKenzie

(10) Patent No.: US PP23,524 P2
(45) Date of Patent: Apr. 9, 2013

(54) ***BRUNNERA* PLANT NAMED 'NONURB'**

(50) Latin Name: *Brunnera macrophylla*
Varietal Denomination: Nonurb

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 0 days.

(21) Appl. No.: 13/374,970

(22) Filed: Jan. 25, 2012

(51) Int. Cl.
*A01H 5/00* (2006.01)

(52) U.S. Cl. ..... Plt./412

(58) Field of Classification Search ..... Plt./412
See application file for complete search history.

*Primary Examiner* — Annette Para
(74) *Attorney, Agent, or Firm* — Penny J. Aguirre

(57) ABSTRACT

A new cultivar of *Brunnera macrophylla*, 'Nonurb', characterized by its foliage that matures with blue-gray centers and green margins with a thin strip of creamy white between the center and margin coloration and a thin white margin on the outer edge, and its leaf venation that is not distinct from the leaf coloration.

2 Drawing Sheets

Botanical classification: *Brunnera macrophylla.*
Cultivar designation: 'Nonurb'.

BACKGROUND OF THE INVENTION

The present invention relates to a new and distinct cultivar of *Brunnera macrophylla*, and is hereinafter referred to by the cultivar name 'Nonurb'. 'Nonurb' represents a new herbaceous perennial grown for use as a landscape plant.

The inventor discovered the new cultivar, 'Nonurb', in July of 2011 as a naturally occurring chimeral mutation *Brunnera macrophylla* 'Jack Frost' (U.S. Plant Pat. No. 13,859) that was growing in a container in a production block of 'Jack Frost' in Nunica, Mich.

Asexual reproduction of the new cultivar was first accomplished by the Inventor by crown division in September of 2011 in Nunica, Mich. Propagation by crown division and tissue culture has determined the characteristics to be stable and reproduced true to type in successive generations.

SUMMARY OF THE INVENTION

The following traits have been repeatedly observed and represent the characteristics of the new cultivar. These attributes in combination distinguish 'Nonurb' as a new and unique cultivar of *Brunnera.*

1. 'Nonurb' exhibits foliage that matures with blue-gray centers and green margins with a thin strip of creamy white between the center and margin coloration and a thin white margin on the outer edge.
2. 'Nonurb' exhibits leaf venation coloration that is not distinct from the leaf coloration.

'Nonurb' can be most closely compared to its parent plant, 'Jack Frost'. 'Jack Frost' differs from 'Nonurb' in having foliage with silvery white-coated centers, green margins, and prominent green venation. 'Nonurb' can be most closely compared to the cultivars 'Variegata' (not patented) and 'Emerald Mist' (U.S. Plant Pat. No. 20,460). 'Variegata' differs from 'Nonurb' in having foliage with green centers, broad white margins, and green venation. 'Emerald Mist' has foliage that is bluish green with dense silver baring on the outer portion of the leaf blade and a silver dusting between the veins.

BRIEF DESCRIPTION OF THE DRAWING

The accompanying colored photographs illustrate the overall appearance and distinct characteristics of the new *Brunnera*. The photographs were taken of a plant about one year in age as grown outdoors in a one-gallon container.

The photograph in FIG. 1 provides a side view of young spring foliage of 'Nonurb'.

Figure 1:
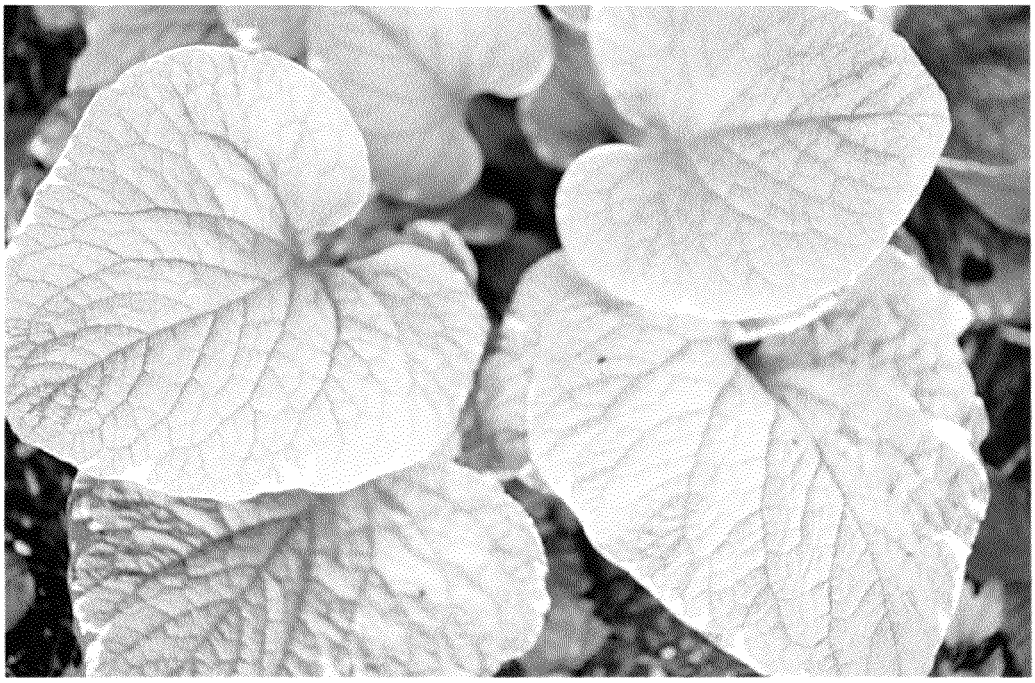
Figure 2:
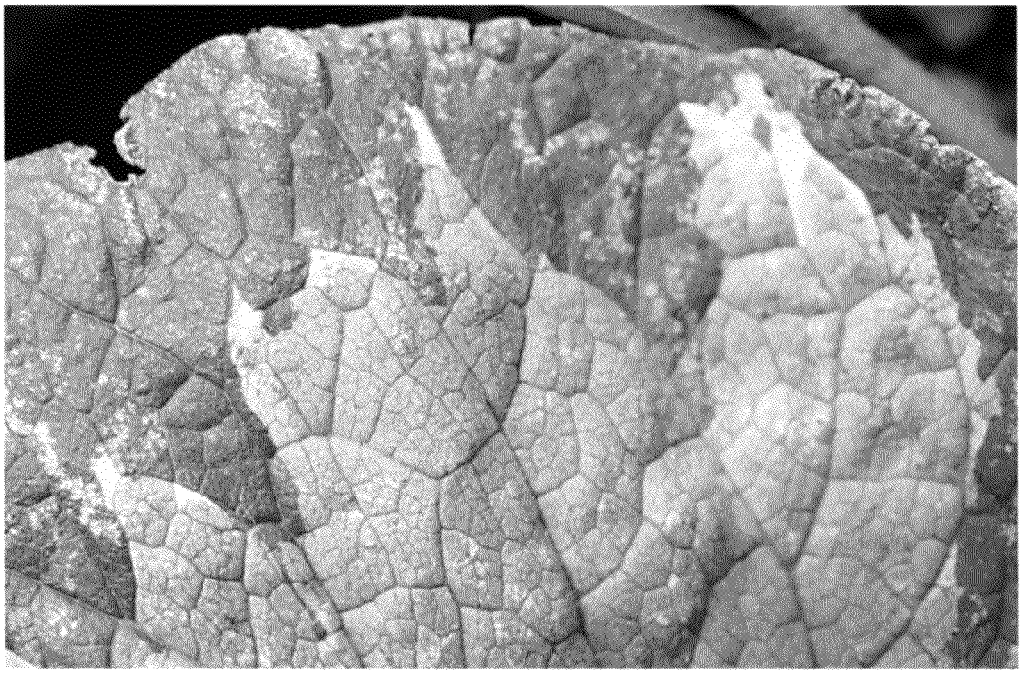

The photograph in FIG. 2 provides a close-up view of a portion of a mature leaf of 'Nonurb'. The colors in the photographs may differ slightly from the color values cited in the detailed botanical description, which accurately describe the colors of the new *Brunnera.*

DETAILED BOTANICAL DESCRIPTION OF THE PLANT

The following is a detailed description of one year-old plants of the new cultivar as grown outdoors in one-gallon containers in Nunica, Mich. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit.*—Blooms in May in Michigan.

*Plant habit.*—Clump-forming herbaceous perennial, open mound with flowering stems emerging from basal rosette of foliage.

*Height and spread.*—Reaches 30 to 38 cm in height and about 60 cm in width.

*Cold hardiness.*—U.S.D.A. Zone 3.

*Diseases and pests.*—No more susceptibility or resistance to diseases or pests than other cultivars of *Brunnera.*

*Root description.*—Fibrous roots on woody rootstalks.

*Branching habit*.—Basal rosettes.

*Propagation*.—In vitro propagation is the preferred method.

*Growth rate*.—Moderately vigorous.

Foliage description:

*Leaf shape*.—Reniform.

*Leaf division*.—Simple.

*Leaf base*.—Deeply cordate.

*Leaf apex*.—Acute to cuspidate.

*Leaf venation*.—Laciniate, slightly conspicuous, color on mature leaves upper surface; 147A, color on mature leaves lower surface; 138B.

*Leaf margins*.—Slightly crenate with broad crenations (an average of 3 cm in length on mature leaves) with short stiff hairs.

*Leaf attachment*.—Petiolate.

*Leaf arrangement*.—Basal rosettes.

*Leaf orientation*.—Held nearly horizontal to petiole, leaf plane is flat to convex with edges occasionally curving downward.

*Leaf surface*.—Upper surface is slightly pubescent with short strigose hairs, dull, and rough to touch, lower surface is densely puberulent with veins pubescent with short strigose hairs.

*Leave variegation pattern*.—Large centers are grey-green (lacks a silver overlay) with green margins that are slightly irregularly mottled with creamy white, a thin white margin between the center and margin, and a very thin white margin on the leaf edge.

*Leaf color*.—Young upper surface leaves; 189C with a thin edge of 155A, mature leaves upper surface; primarily 189C, margin area is 137A and irregularly mottled with 138C and a few spots of 155A, with a stripe of 155A between the margins and centers and a thin margin on the leaf edge of 155A, young and mature leaves lower surface; 191A with margin area mottled with 155A and occasional regions of 146C.

*Leaf size*.—Mature to average of 22 cm in length and width.

*Leaf quantity*.—Average of 19 per one year-old plant.

*Petioles*.—Average of 12 cm in length and 3.5 mm in width, 146B in color, sulcate in shape, surface is dull and pubescent with short stiff fine hairs.

Flower description:

*Inflorescence type*.—Terminal paniculate cymes of rotate flowers on leafy flowering stems that arise from base with smaller panicles from upper nodes.

*Flowering stems*.—Average of 30 cm in length and 3 mm in width, color is 138B, surface is pubescent with hairs 155B in color and 0.5 mm in length, cauline leaves; average of 3, spatulate in shape, sessile, average of 8 cm in length and 7.5 cm in width, acute apex, cuneate base, color, venation and surface match basal leaves.

*Inflorescence size*.—Average of 45 cm in height (including peduncle) and about 10 cm in width.

*Flower fragrance*.—None detected.

*Flower quantity*.—Average of 4 flowering stems per one-gallon sized plant, average of 100 flowers per flowering stem.

*Flower Lastingness*.—Average of 7 days per flower, individual panicles blooms for about 3 weeks.

*Flower buds*.—Globose in shape, average of 2.5 mm in diameter and depth, calyx portion is 137D with apex 76B.

*Flower aspect*.—Held horizontal to pedicles held at about a 45° angle from peduncle.

*Flower size*.—Average of 7 mm in diameter and 5 mm in depth.

*Petals*.—5, broadly oblanceolate in shape, fused at base, margin is entire, apex is acute, upper and lower surface is glabrous, color is 106B on upper surface and 108B on lower surface, about 3 mm in length and width.

*Calyx*.—Campanulate with sepals fused at base, about 3.5 mm in width and 1.5 mm in length.

*Sepals*.—5, lanceolate in shape, about 1.5 mm in length and 0.4 mm width, margin is entire, apex is acute, base is fused, surface pubescent, color of upper and lower surface is 138A.

*Peduncles*.—Average of 2 cm in length and 1.5 mm in width on individual cymes, pubescent surface, color 138B.

*Pedicels*.—Average of 5 mm in length and about 1 mm in width, pubescent surface, color 138B.

Reproductive organs:

*Gynoecium*.—1 Pistil, about 4 mm in length and <0.3 mm in width, stigma about 0.25 mm in width and length, ovary superior and about 0.5 mm in diameter and height, style and stigma 193D in color, and ovary 155B in color.

*Androcoecium*.—5 stamens, included, basifixed, about 2.5 mm in length and 10.7 mm in width and 155B in color, anthers about 0.5 mm in length and 187A in color, pollen 158D in color.

*Seed*.—Nutlet, about 0.7 mm in diameter, 200A in color.

It is claimed:

1. A new and distinct cultivar of *Brunnera* plant named 'Nonurb' as herein illustrated and described.

* * * * *